United States Patent
Popelar et al.

(10) Patent No.: US 6,571,856 B1
(45) Date of Patent: Jun. 3, 2003

(54) METHOD FOR PREDICTING THE MICROSTRUCTURE OF SOLIDIFYING CAST IRON

(75) Inventors: Patrik Popelar, Katrineholm (SE); Conny Andersson, Eskilstuna (SE)

(73) Assignee: Sintercast AB, Stockholm (SE)

( * ) Notice: Subject to any disclaimer, the term of this patent is extended or adjusted under 35 U.S.C. 154(b) by 0 days.

(21) Appl. No.: 09/868,066
(22) PCT Filed: Dec. 16, 1999
(86) PCT No.: PCT/SE99/02393
§ 371 (c)(1),
(2), (4) Date: Jun. 14, 2001
(87) PCT Pub. No.: WO00/37699
PCT Pub. Date: Jun. 29, 2000

(30) Foreign Application Priority Data

Dec. 18, 1998 (SE) .............................................. 9804419
Jun. 24, 1999 (SE) .............................................. 9902407

(51) Int. Cl.$^7$ .............................................. B22D 27/20
(52) U.S. Cl. ...................................... 164/4.1; 164/58.1
(58) Field of Search ................................ 164/4.1, 57.1, 164/58.1, 151.4, 154.1, 154.6

(56) References Cited

U.S. PATENT DOCUMENTS 5,949,000 A * 9/1999 Lindholm et al. .......... 374/139

FOREIGN PATENT DOCUMENTS

| DE | 29 49 598 | 6/1979 |
|----|-----------|--------|
| SE | 9704411-9 | 5/1999 |
| WO | WO 86/01755 | 3/1986 |
| WO | WO 91/13176 | 9/1991 |
| WO | WO 92/06809 | 4/1992 |
| WO | WO 99/25888 | 5/1999 |

OTHER PUBLICATIONS

Transactions of the American Foundrymen's Society, Volym 92, Apr. 1984, I–G.Chen et al. "Computer–aided differential Thermal Analysis of Spheroidal and Compacted Graphite Cast Iron", pp. 947–964, p. 950, col. 1, line 17–p. 955, col. 1, Line 10.

Gjuteriet, Volym, No. 3, 1996, Jon Nilsson, "Utvecklingsprojekt pa Segjarnsomradet for optimerad gjutgodskvalitet" pp. 18–19.

* cited by examiner

*Primary Examiner*—Kuang Y. Lin
(74) *Attorney, Agent, or Firm*—Pillsbury Winthrop LLP

(57) ABSTRACT

By studying heat transfer in a sample vessel containing a sample of molten cast iron, it is possible to carry out accurate predictions of the microstructure in which the molten cast iron sample will solidify. This method is also highly suitable for automatisation by using a computer.

8 Claims, 5 Drawing Sheets

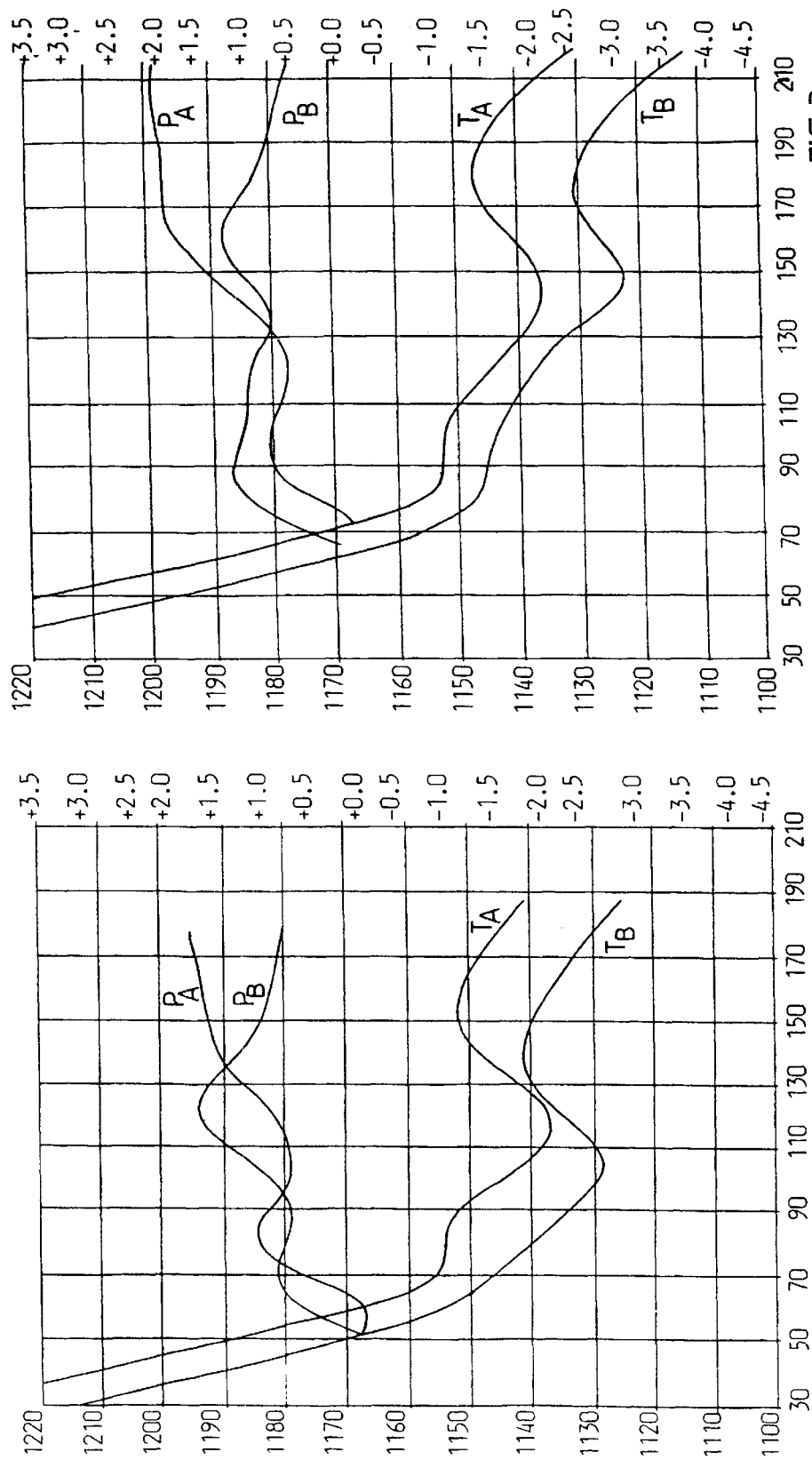

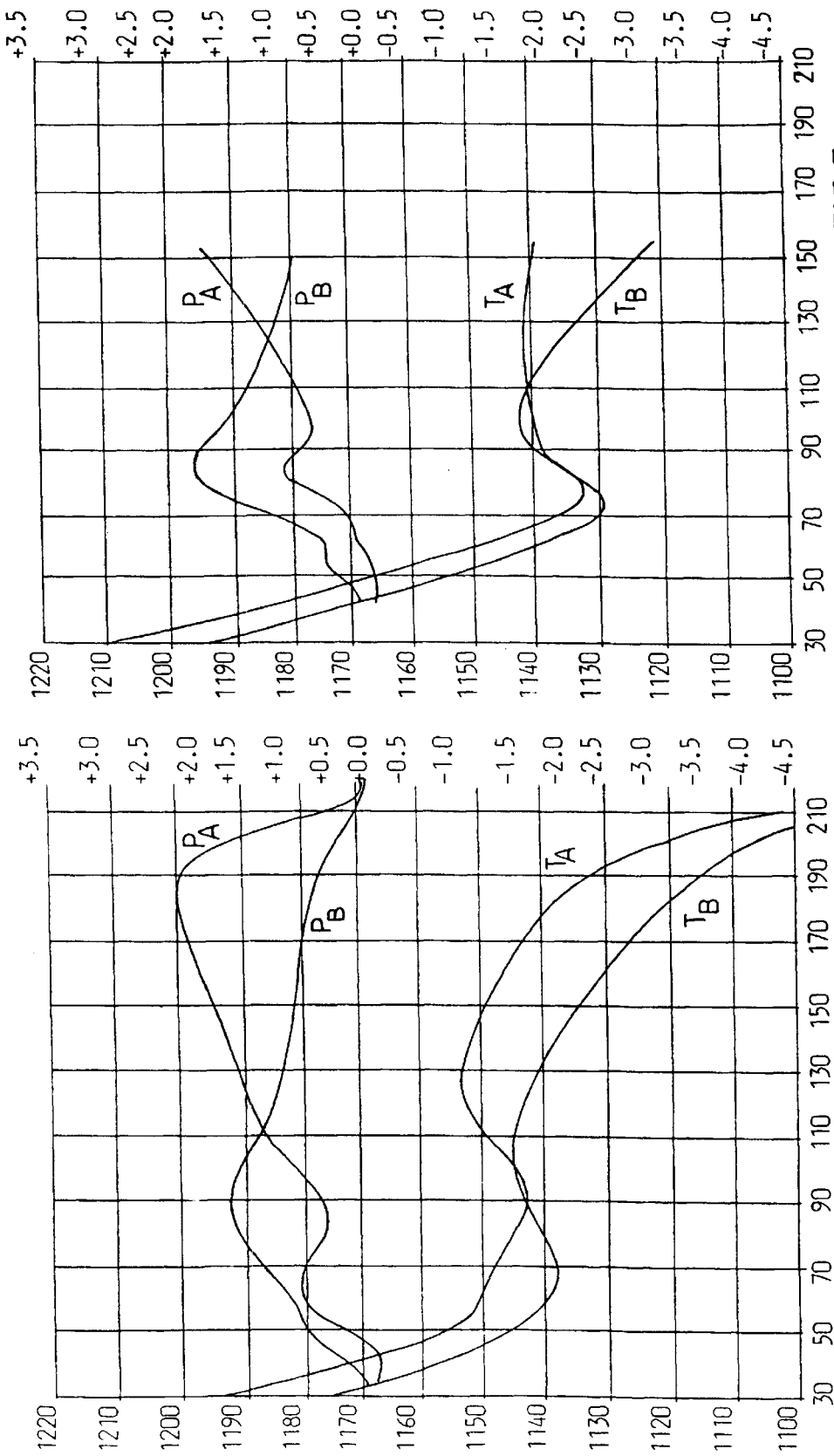

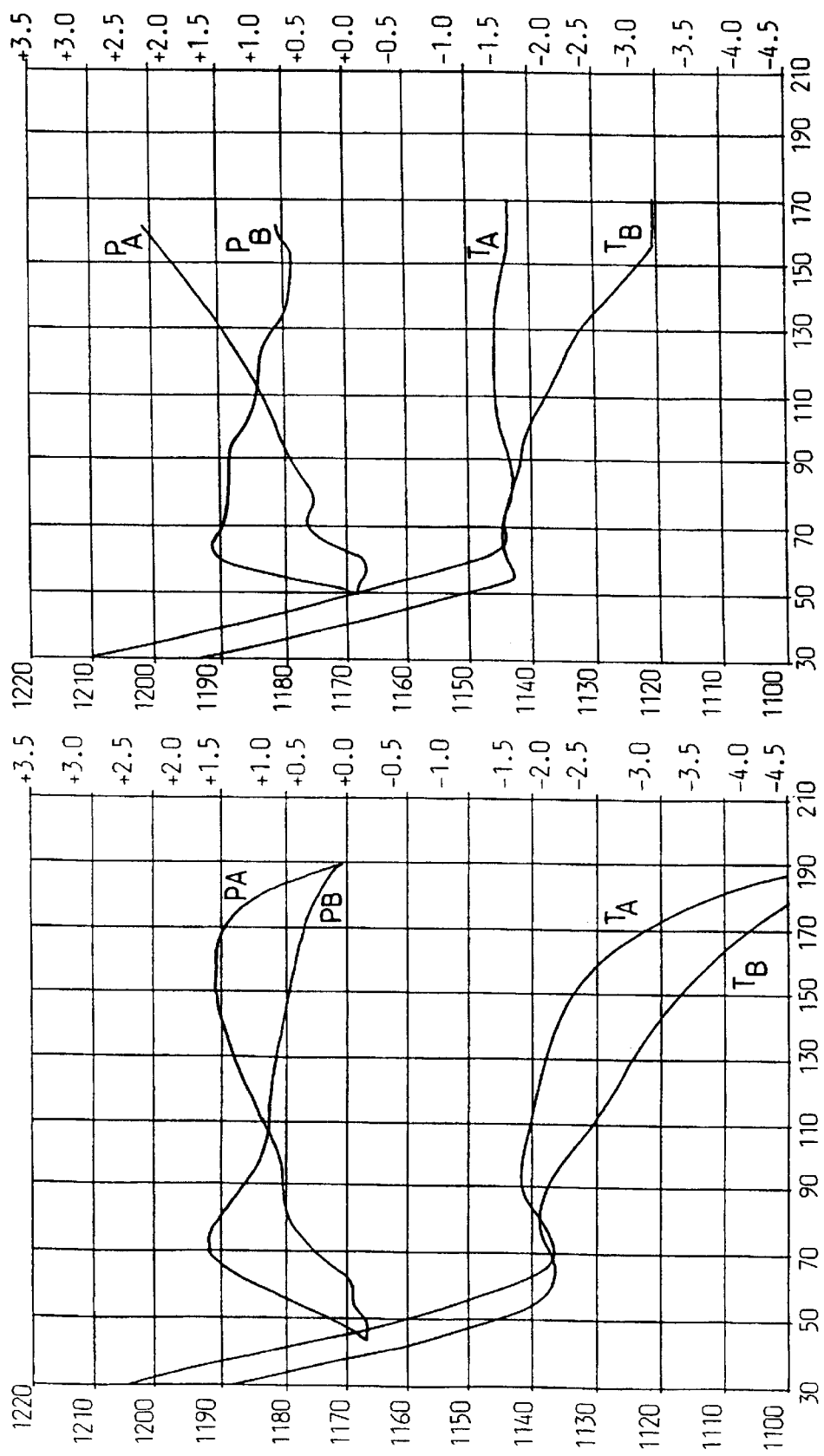

METHOD FOR PREDICTING THE MICROSTRUCTURE OF SOLIDIFYING CAST IRON

This application is the National Phase of International Application PCT/SE99/02393 filed Dec. 16, 1999 which designated the U.S. and that International Application was published under PCT Article 21(2) in English.

BACKGROUND OF THE INVENTION

1. Field of the Invention

The present invention relates to an improved method for predicting the microstructure with which a certain cast iron melt will solidify. The invention also relates to an apparatus for carrying out the method.

2. Description of Related Art

WO86/01755 (incorporated by reference) discloses a method for producing compacted graphite cast iron by using thermal analysis. A sample is taken from a bath of molten cast iron and this sample is permitted to solidify during 0.5 to 10 minutes. The temperature is recorded simultaneously by two temperature responsive means, one of which is arranged in the centre of the sample and the other in the immediate vicinity of the vessel wall. So-called cooling curves representing temperature of the iron sample as a function of time are recorded for each of the two temperature responsive means. According to this document it is then possible to determine the necessary amount of structure-modifying agents that must be added to the melt in order to obtain the desired microstructure.

WO92/06809 (incorporated by reference) describes a specific method for evaluating the cooling curves obtained by the method of WO86/01755. According to this document, thermal analysis is carried out in a sample vessel coated with a material consuming the active form of the structure-modifying agent. This material may comprise oxides of Si, Mn, Fe, K and Na. An early plateau in the cooling curve recorded by a certain temperature-responsive means located near the vessel wall indicates that flake graphite has been formed due to interaction with the coating. It is then possible to determine whether any structure-modifying agent has to be added to the melt in order to obtain compacted graphite cast iron by using calibration data.

When casting compacted graphite cast iron in a commercial large-scale foundry, it is of utmost importance that accurate and reliable predictions of the micro-structure of the castings can be carried out. Sometimes cooling curves that are difficult to interpret are accepted as CGI despite the fact that some flaky graphite has been formed. In order to improve the accuracy of the evaluation, there is thus a need for alternative methods for evaluating cooling curves which methods can compensate for deviations from the normal appearance of the cooling curves.

SUMMARY OF THE INVENTION

Now, it has turned out that by studying heat transfer in a sample vessel containing a sample of molten cast iron, it is possible to carry out accurate predictions of the microstructure in which the molten cast iron sample will solidify. This method is also highly suitable for automatization by using a computer.

DEFINITIONS

The term "cooling curve" as disclosed herein refers to graphs representing temperature as a function of time, which graphs have been recorded in the manner disclosed in WO86/01755 and WO92/06809.

The term "heat generation curve" as utilised herein relates to a graph showing the heat that is generated in a certain zone of a molten cast iron as a function of time. For the purposes of the present invention, the heat generation curves herein are determined for a zone located in the centre of a molten cast iron sample (the A zone), and in the periphery of a molten cast iron sample (the B zone), respectively. Below, methods for determining heat generation curves will be further described.

The term "sample vessel" as disclosed herein, refers to a small sample container which, when used for thermal analysis, is filled with a sample of molten metal. The temperature of the molten metal is then recorded during solidification in a suitable way. Preferably the sample vessel is designed in the manner disclosed in WO86/01755, WO92/06809, WO91/13176 (incorporated by reference), WO96/23206 (incorporated by reference) or PCT/SE98/02122.

The term "sampling device" as disclosed herein, refers to a device comprising a sample vessel equipped with at least two temperature responsive means for thermal analysis, said means being intended to be immersed in the solidifying metal sample during analysis, and a means for filling the sample vessel with molten metal. The sample vessel is preferably equipped with said sensor in the manner disclosed in FIG. 2 in WO96/23206 or PCT/SE98/02122.

The term "structure-modifying agent" as disclosed herein relates to compounds affecting the morphology of graphite present in the molten cast iron. Suitable compounds can be chosen from the group of magnesium and rare earth metals such as cerium, or mixtures of these compounds. The relationship between the concentration of structure-modifying agents in molten cast irons have already been discussed in the above cited documents WO92/06809 and WO86/01755.

The term "CGI" as disclosed herein refers to compacted graphite cast iron.

The term "SGI" as disclosed herein refers to spheroidal graphite cast iron.

BRIEF DESCRIPTION OF THE DRAWINGS

The invention will now be described with reference to the accompanying figures in which:

FIG. 2 discloses cooling curves and corresponding heat generation curves for CGI. In FIGS. 2–7, the following abbreviations are used; $T_A$=centrally recorded cooling curve, $T_B$=peripherically recorded cooling curve, $P_A$=heat generation in the centre, and $P_B$=heat generation in the periphery;

FIG. 3 discloses cooling curves and corresponding heat generation curves for a low nodularity CGI. During the measurement flake graphite is formed in the sample vessel due to reaction with the wall coating;

FIG. 4 discloses cooling curves and corresponding heat generation curves for cast iron comprising a high carbon equivalent content;

FIG. 5 discloses cooling curves and corresponding heat generation curves for a near eutectic iron;

FIG. 6 discloses cooling curves and corresponding heat generation curves for a eutectic or hypereutectic iron; and FIG. 7 discloses cooling curves and corresponding heat generation curves for grey flake iron.

DETAILED DESCRIPTION OF THE INVENTION

As already disclosed above, the present invention relates to predicting the micro-structure in which a certain molten cast iron sample will solidify by measuring the heat evolution in the sample. In particular, the invention relates to determining the heat transfer between two sample zones (one zone in the centre of the sample and one peripheral zone encompassing the central zone) and the surroundings. By studying graphs presenting the derivative of heat as a function of time, it is possible to carry out accurate predictions.

The thermal balance of any uniform element can be described by the relation:

$$Q_{stored} = Q_{generated} + Q_{in} - Q_{out} \tag{1}$$

where $Q_{stored}$ is the amount of heat stored by the heat capacity of the material, $Q_{generated}$ is the amount of heat generated by the volume of material, $Q_{in}$ is the heat transferred into the material from its surroundings and $Q_{out}$ is the heat transferred from the sample volume to its surroundings.

Figure 1:
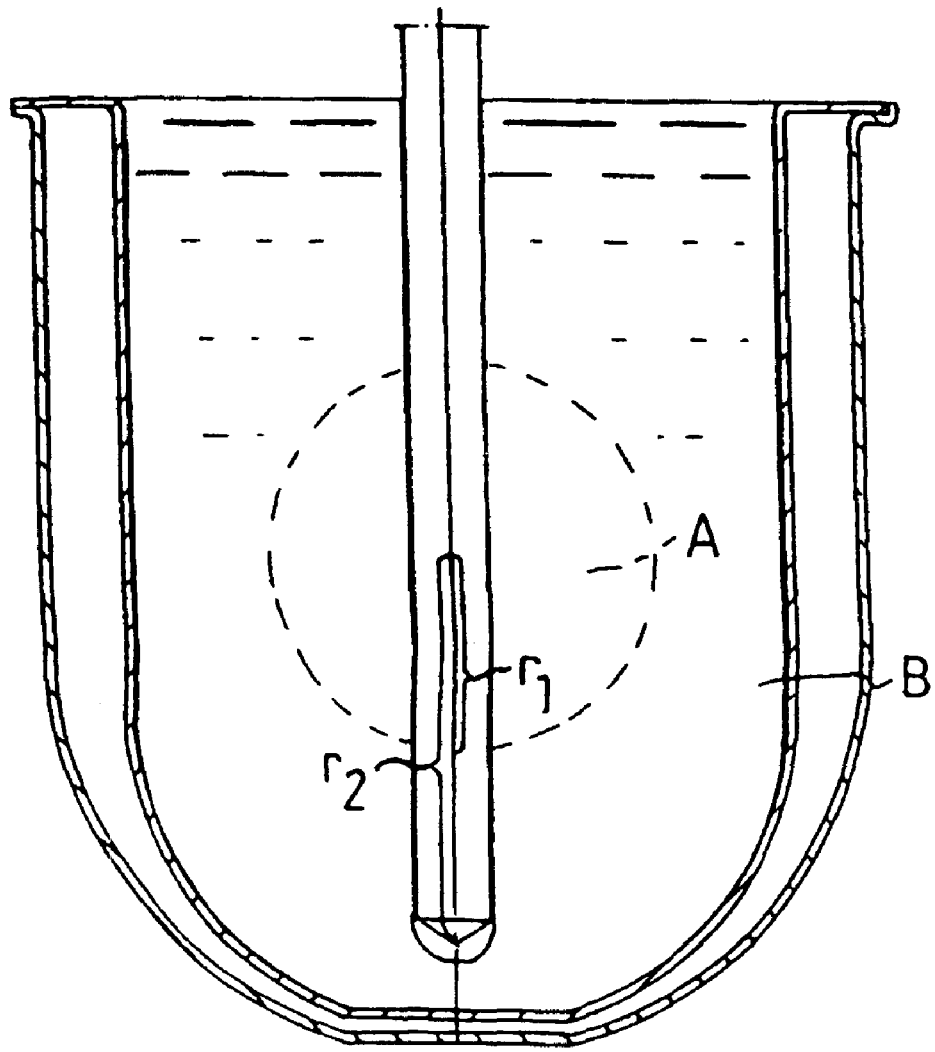
FIG. 1 schematically outlines a diagram of a sample vessel that can be used in connection with the present invention. In such a sample vessel the heat is uniformly transported in all directions. A sample of molten cast iron comprised in such a vessel can therefore be regarded as a freezing sphere. In this figure, the freezing sphere is divided into two zones A and B. The radii $r_1$ and $r_2$ relate to the average radii of zones A and B, respectively.

When carrying out the present invention, it is advantageous to use a sample vessel as disclosed in SE 9704411-9. In such a sample vessel, the heat transport in a sample contained in the vessel is approximately the same in all directions. From now on, the heat transport between the centre (FIG. 1, zone A) and the more peripheral part (FIG. 1, zone B) of the molten cast iron contained in a sample vessel is described. As the A zone is situated in the centre of the freezing sphere, no heat will be transported into the zone and $Q_{in}$ is therefore equal to zero. Appropriate substitutions in relation (1) above give the following equation:

$$C_p m_A dT_A/dt = Q_{genA} + 0 - 4\pi ke[(T_A-T_B)/(1/r_1-1/r_2)] \tag{2}$$

where $C_p$ is the heat capacity per unit mass, $m_A$ is the mass of the A zone, $dT_A/dt$ is the temperature change of the A zone per unit time, ke is the effective heat transfer coefficient of the material, and $(1/r_1-1/r_2)^{-1}$ is the mean distance for heat transport. The radii $r_1$ and $r_2$ are both defined in FIG. 1. $T_A$ and $T_B$ are the temperatures in the A zone and B zone, respectively.

From equation (2) we can isolate the heat generation term and calculate the average bulk heat generation in the A zone:

$$Q_{genA} = C_p m_A dT_A/dt + 4\pi\, ke[(T_A-T_B)/(1/r_1-1/r_2)] \tag{3}$$

In equation (3) all variables are constants except $dT_A/dt$ and $(T_A-T_B)$. Accordingly, equation (3) can be simplified to:

$$Q_{genA} = k_1 dT_A/dt + k_2(T_A-T_B) \tag{4}$$

where $k_1$ and $k_2$ are constants. Hence a heat generation curve corresponding to the A zone can be calculated from a set of cooling curves recorded in the centre and periphery of a sample of molten cast iron.

Heat balance for the B zone resembles the balance of zone A, but heat is transferred both into the zone (from the A zone) and out from it (to the surroundings). Hence term $Q_{in}$ in relation (1) is not equal to zero. Appropriate substitutions in relation (1) give the following equation:

$$C_p m_B dT_B/dt = Q_{genB} + 4\pi ke[(T_A-T_B)/(1/r_1-1/r_2)] - [h(T_B-T_S) + \epsilon A_B \sigma(T_B^4 - T_S^4)] \tag{5}$$

where, in addition to those variables defined in connection with equations (2) and (3) above, h is the convective heat loss to the surroundings, $T_S$ is the temperature of the surroundings, and $\epsilon A_B \sigma$ is the appropriate constant in Stefan-Boltzmann law of radiation.

Regarding the last term, we can assume that the ratio between total radiative heat loss and convective heat loss is constant:

$$C = \epsilon A_B / h \tag{6}$$

Accordingly, we can isolate the heat generation term of zone B, $Q_{genB}$:

$$Q_{genB} = C_p m_B dT_B/dt - 4\pi ke[(T_A-T_B)/(1/r_1-1/r_2)] + h[(T_B-T_S) + C\sigma(T_B^4-T_S^4)] \tag{7}$$

In equation (7) all variables are constant except $dT_B/dt$, $(T_A-T_B)$ and $T_B$. Accordingly, equation (7) can be simplified to:

$$Q_{genB} = k_3 dT_B/dt - k_4(T_A-T_B) + k_5 T_B + k_6 T_B^4 - k_7 \tag{8}$$

By applying equations (4) and (8) on cooling curves recorded in the manner disclosed in WO86/01755 and WO92/06809 we can determine the corresponding heat generation curves. FIGS. 2A–6A disclose different kinds of cooling curves and FIGS. 2B–6B corresponding heat generation curves.

As already mentioned, these calculations are based on a situation where heat is uniformly transported in all directions. The skilled person can of course determine other equations corresponding to other heat transport conditions.

There are larger differences between different kinds of heat generation curves compared to corresponding cooling curves. For CGI (FIG. 2), the curve representing heat release in the B zone comprises two distinct peaks, one smaller and one larger, whereas the heat release for low nodularity CGI (FIG. 3) is so much larger that these two peaks hardly can be separated. This also applies to curves related to high carbon equivalent cast iron (FIG. 4). A primary austenite peak is visible the A zone curve. In heat generation curves representing near eutectic iron (FIG. 5) a small austenite peak is still visible, whereas the peak has disappeared in the curves relating to eutectic or hypereutectic iron (FIG. 6). As regards grey flaky iron (FIG. 7), the first peak of the heat generation curve representing the B zone is dominating.

Figure 8:
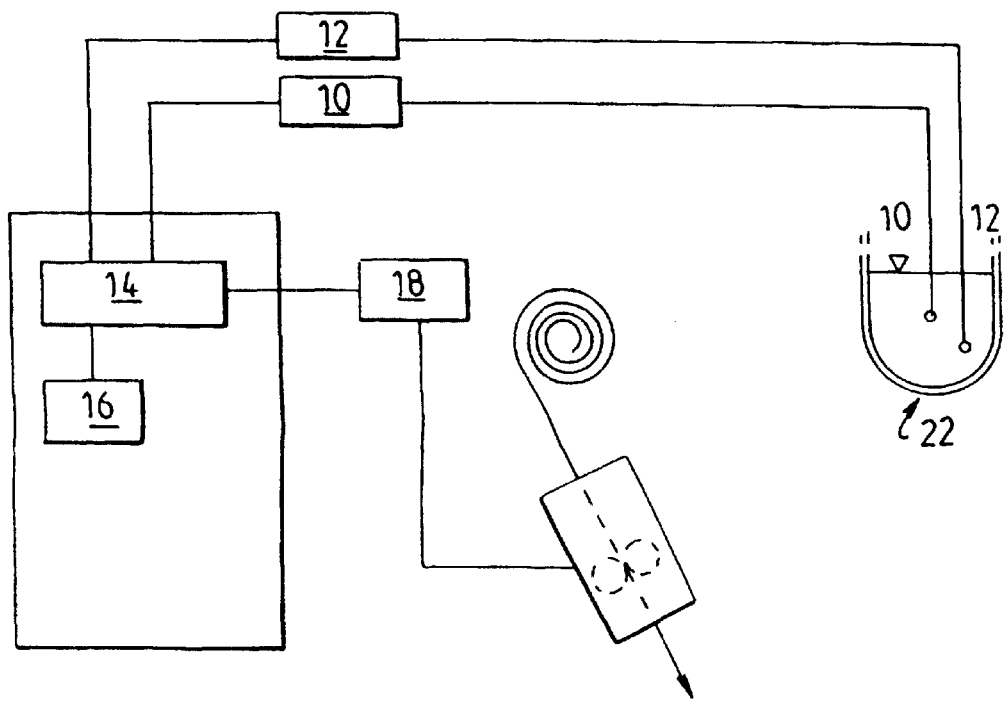
FIG. 8 is a schematic presentation of an apparatus for controlling production of compacted graphite cast iron according to the present invention.

It is preferred to carry the prediction method by using a computer-controlled system, especially when a large number of measurements must be carried out. Such a system is outlined in FIG. 8. A sample of a molten cast iron is taken and transferred to a sample vessel 22. During the measurement of a particular sample the two temperature-responsive means 10,12 send signals to a computer means 14 in order to generate cooling curves and corresponding heat generation curves, e.g. by applying equations (3) and (6). The computer has access to calibration data, e.g. previously recorded model curves corresponding to a known amount of structure-modifying agent or a known microstructure, in a ROM unit 16 and calculates the amount of structure-modifying agent that has to be added to the melt. In a preferred embodiment this is implemented as an expert system. The amount of structure-modifying agent to be added is signalled to a means 18 for administrating structure-modifying agent to the melt 20 to be corrected, whereby the melt is supplied with an appropriate amount of such agents.

What is claimed is:

1. A process for producing a CGI casting or optionally a SGI casting, requiring a sampling device, at least two means for recording cooling curves, and a means for administering structure-modifying agent(s) to a molten cast iron from which said casting is to be produced, said method comprising:
   a) providing a sample of the molten cast iron from which said casting is to be produced, and adding said sample to a sample vessel;
   b) simultaneously recording at least two cooling curves, at distances $r_1$ and $r_2$, etc., from the centre of the sample vessel;
   c) determining at least two heat generation curves by using the information obtained in b), wherein each one of the at least two heat generation curres depends upon the at least two cooling curves;
   d) comparing the heat generation curves obtained in c) with previously determined heat generation curves representing known concentrations of structure-modifying agents which previously determined heat generation curves have been obtained under same conditions as in step a), b) and c);
   e) determining the amount of structure-modifying agent to be added to the melt based upon the comparison in step d);
   f) causing said means for administrating structure-modifying agent to administrate a correct amount to the melt; and
   g) carrying out the casting operation.

2. A process according to claim 1, wherein said sample vessel is of a type wherein heat is substantially uniformly transported in all directions when it is filled with molten cast iron.

3. A process according to claim 1 or claim 2, wherein compacted graphite cast iron is produced.

4. A process for determining the amount of structure-modifying agent that has to be added to a certain cast iron melt in order to obtain CGI or optionally SGI, requiring a sampling device, and at least two means for recording cooling curves, said method comprising:
   a) providing a sample of the molten cast iron from which said casting is to be produced, and adding said sample to a sample vessel;
   b) simultaneously recording at least two cooling curves, at distances $r_1$ and $r_2$, etc., from the centre of the sample vessel;
   c) determining at least two heat generation curves by using the information obtained in b), wherein each one of the at least two heat generation curves depends cooling curves;
   d) comparing the heat generation curves obtained in c) with previously determined heat generation curves representing known concentrations of structure-modifying agents which previously determined heat generation curves have been obtained under same conditions as in step a), b) and c); and
   e) determining the amount of structure-modifying agent to be added to the melt based upon the comparison in step d).

5. A process for producing a CGI casting or optionally a SGI casting, said method comprising:
   a) providing a sample of the molten cast iron from which said casting is to be produced, and adding said sample to a sample vessel;
   b) simultaneously recording at least two cooling curves, at distances $r_1$ and $r_2$, etc., from the centre of the sample vessel;
   c) determining at least two heat generation curves by using the information obtained in b), wherein each one of at least two heat generation curves depends upon the at least two cooling curves;
   d) comparing the heat generation curves obtained in c) with previously determined heat generation curves representing known concentrations of structure-modifying agents which previously determined heat generation curves have been obtained under same conditions as in step a), b) and c);
   e) determining the amount of structure-modifying agent to be added to the melt based upon the comparison in step d);
   f) administrating a correct amount of at least one structure-modifying agent to the melt; and
   g) carrying out the casting operation.

6. A process according to claim 1, wherein said sample vessel is of a type wherein heat is substantially uniformly transported in all directions when it is filled with molten cast iron.

7. A process according to claim 1, wherein compacted graphite cast iron is produced.

8. A process for determining the amount of structure-modifying agent that has to be added to a certain cast iron melt in order to obtain CGI or optionally SGI, said method comprising:
   a) providing a sample of the molten cast iron from which said casting is to be produced, and adding said sample to a sample vessel;
   b) simultaneously recording at least two cooling curves, at distances $r_1$ and $r_2$, etc., from the centre of the sample vessel;
   c) determining at least two heat generation curves by using the information obtained in b), wherein each one of the at least two heat generation curves depends upon the at least two cooling curves;
   d) comparing the heat generation curves obtained in c) with previously determined heat generation curves representing known concentrations of structure-modifying agents which previously determined heat generation curves have been obtained under same conditions as in step a), b) and c); and
   e) determining the amount of structure-modifying agent to be added to the melt based upon the comparison in step d).

* * * * *